(12) United States Patent
Lindner

(10) Patent No.: US 10,634,606 B2
(45) Date of Patent: Apr. 28, 2020

(54) ARRANGEMENT FOR MEASURING GAS CONCENTRATIONS

(71) Applicant: bluepoint medical GmbH & Co. KG, Selmsdorf (DE)

(72) Inventor: Bernd Lindner, Stockelsdorf (DE)

(73) Assignee: bluepoint medical GmbH & Co. KG, Selmsdorf (DE)

(*) Notice: Subject to any disclaimer, the term of this patent is extended or adjusted under 35 U.S.C. 154(b) by 319 days.

(21) Appl. No.: 15/638,987

(22) Filed: Jun. 30, 2017

(65) Prior Publication Data
US 2018/0011007 A1 Jan. 11, 2018

(30) Foreign Application Priority Data
Jul. 11, 2016 (EP) .................................. 16178808

(51) Int. Cl.
*G01N 21/17* (2006.01)
*G01N 21/31* (2006.01)
(Continued)

(52) U.S. Cl.
CPC ........ *G01N 21/1717* (2013.01); *G01J 3/0205* (2013.01); *G01J 3/0216* (2013.01);
(Continued)

(58) Field of Classification Search
CPC ............. G01N 21/1717; G01N 21/256; G01N 2201/121; G01N 2201/1218;
(Continued)

(56) References Cited

U.S. PATENT DOCUMENTS

| 7,063,667 B1* | 6/2006 | Ben-Oren | ............ A61B 5/0836 422/84 |
| 2006/0034071 A1* | 2/2006 | Wang | ........................ F21S 8/00 362/157 |

(Continued)

FOREIGN PATENT DOCUMENTS

| DE | 102008064173 | 7/2010 |
| DE | 102011116367 A1 | 4/2013 |

OTHER PUBLICATIONS

Rabe, Marian et al., "Mode filter for LED-based absorption spectroscopy," May 23, 2016, pp. 1-5.
(Continued)

*Primary Examiner* — Robert R Raevis
(74) *Attorney, Agent, or Firm* — Murtha Cullina LLP

(57) ABSTRACT

An arrangement for measuring gas concentrations in a gas absorption method, wherein the arrangement includes a plurality of light sources, a measuring cell, at least one measuring receiver and an evaluation apparatus. The measuring cell has a narrow, longitudinally-extended beam path with an entrance-side opening diameter B and an absorption length L with L>B, wherein the measuring cell has a gas inlet and a gas outlet wherein a plurality of light sources of different wavelength spectra is grouped into a first light source group wherein an optical homogeniser is interposed between the first light source group and the measuring cell, wherein, in particular, the homogeniser is coupled to the light source group directly or via a common optical assembly.

19 Claims, 4 Drawing Sheets

(51) Int. Cl.

| | |
|---|---|
| *G02B 6/00* | (2006.01) |
| *G01J 3/10* | (2006.01) |
| *G01J 3/42* | (2006.01) |
| *G01N 33/00* | (2006.01) |
| *G01J 3/02* | (2006.01) |
| *F21V 8/00* | (2006.01) |
| *G01N 21/25* | (2006.01) |
| *G01N 21/01* | (2006.01) |
| *G01N 21/45* | (2006.01) |

(52) U.S. Cl.
CPC . *G01J 3/10* (2013.01); *G01J 3/42* (2013.01); *G01N 21/256* (2013.01); *G01N 21/314* (2013.01); *G01N 33/0037* (2013.01); *G01N 33/0042* (2013.01); *G02B 6/00* (2013.01); *G02B 6/0068* (2013.01); *G01J 2003/102* (2013.01); *G01N 2021/0106* (2013.01); *G01N 2021/1704* (2013.01); *G01N 2021/1736* (2013.01); *G01N 2021/1742* (2013.01); *G01N 2021/1748* (2013.01); *G01N 2021/3155* (2013.01); *G01N 2021/3181* (2013.01); *G01N 2021/451* (2013.01); *G01N 2201/0627* (2013.01); *G01N 2201/0631* (2013.01); *G01N 2201/0668* (2013.01); *G01N 2201/0806* (2013.01); *G01N 2201/1211* (2013.01); *G01N 2201/1218* (2013.01); *Y02A 50/245* (2018.01)

(58) Field of Classification Search
CPC .......... G01N 33/0037; G01N 33/0042; G01N 21/314; G01N 2021/0106; G01N 2021/1704; G01N 2021/1736; G01N 2021/1742; G01N 2021/1748; G01N 2021/451; G01N 2021/3155; G01N 2021/3181; G01N 2201/0627; G01N 2201/0631; G01N 2201/0668; G01N 2021/0631; G01N 2201/0806; G01J 3/0205; G01J 3/42; G01J 3/0216; G01J 2003/102; G01J 3/10; G02B 6/00; G02B 6/0068; Y02A 50/245

USPC ........................ 73/23.2, 23.31, 31.05, 28.01; 356/436–440; 250/339.13

See application file for complete search history.

(56) References Cited

U.S. PATENT DOCUMENTS

| | | | |
|---|---|---|---|
| 2010/0252737 A1 | 10/2010 | Fournel et al. | |
| 2012/0006098 A1* | 1/2012 | Degner | G01J 3/02 |
| | | | 73/31.05 |
| 2013/0110311 A1 | 5/2013 | Ver Steeg et al. | |
| 2015/0355082 A1* | 12/2015 | Lu | G01N 21/359 |
| | | | 356/437 |

OTHER PUBLICATIONS

Degner, M. et al., "Real time exhaust gas sensor with high resolution for onboard sensing of harmful components," Oct. 26, 2008, pp. 973-976.

Degner, M. et al., "LED-spectroscopy based on multi quantum well emitter," Sep. 2, 2012, pp. 840-843.

* cited by examiner

ARRANGEMENT FOR MEASURING GAS CONCENTRATIONS

CROSS REFERENCE TO RELATED APPLICATION

The present application claims priority benefit under European Patent Application No. 16 178 808.8 filed on Jul. 11, 2016, the entirety of which is incorporated by reference herein.

FIELD

The invention relates to an arrangement for measuring gas concentrations in a gas absorption method in which light from light sources of various wavelengths in the visible region, the UV region and/or IR region, especially LED light sources, is conducted through a measuring cell with a gas mixture to be analysed, in particular a mixture of $NO_2$, $SO_2$ and/or NO in air, and gas concentrations of gases of the gas mixture to be measured are determined via a measurement of an attenuation of the light conducted into the measuring cell at various wavelengths due to absorption in the various gases of the gas mixture.

RELATED ART

The measurement of gas concentrations by means of a gas absorption method is a known method of measuring technology. It is based on the property of gases to absorb and thereby attenuate light of certain wavelengths. The measurement of the attenuation is then a measurement for the gas concentration of the absorbing gas. The measurement of the attenuation of the light transmission through the gas usually requires a reference measurement, from which, either directly or indirectly, a conclusion can be drawn as to the intensity of the light emitted into the gas.

Known possibilities of a reference measurement include, for example, diverting a portion of the light first emitted, which is then conducted onto an optical measuring receiver without passing through the measuring gas. However, with this direct measurement, no account is taken of the fact that further optical members, such as light inlet windows and light outlet windows of a measuring cell or light conductors, themselves cause an absorbing effect and can become more opaque due to contamination for example.

An alternative possibility for this purpose is provided by using absorption band gaps in the absorption spectrum of the gas to be measured or gases to be measured, in order to conduct light with a wavelength through the measuring cell, which is known not to be absorbed or only slightly absorbed in the measuring gas or the measuring gases. This light suffers the same attenuation in the remaining optical members of such a measuring arrangement as the light which, for example, is adjusted to the absorption maxima of the measuring gases. A measuring effect due to increasing contamination of the measuring cell for example is thus excluded. Noteworthy in this case is the fact that the wavelengths of the reference measurement should not be too different from the wavelengths of the actual absorption measurement since otherwise dispersive effects, that is, wavelength-dependent effects, can play a disturbing role.

An arrangement, with which a corresponding gas absorption method can be carried out, is described in the applicant's patent application, DE 10 2008 064 173 A1, the content disclosed of which should be incorporated into the present application in its entirety. The apparatus shown therein serves, among other things, to measure nitrogen monoxide (NO), nitrogen dioxide ($NO_2$), sulphur dioxide ($SO_2$), ozone ($O_3$) and components in fluid media, for combustion engines, in particular during the online monitoring of diesel engines, in environmental technology or medical technology, for measuring respiratory air for example. In this case, LEDs of various colours are used as light sources, the light of each of which is coupled into an optical fibre.

With this type of light generation and transmission, the fact that LEDs are areal light-generating members and the light generation is not constant over the entire area of the LEDs must be considered. On the contrary, temporally changeable domains form on the LEDs, which emit light and which change over time, for example, wander over the surface of the LED, divide, expire or reunite. The same applies to the direction of radiation, which, although it is generally limited to one radiation cone within an angle of radiation, does however populate the radiation cone in a temporally changeable manner. For this reason, the light generated by the LEDs couples into various modes of the optical fibres. To prevent intensity and the direction of radiation of the light exiting the optical fibres fluctuating at the exit of the optical fibres, according to DE 10 2008 064 173 A1 the modes are mixed such that the light exiting the optical fibres has become independent of the original place and the original direction of the light generation.

An alternative arrangement is known from DE 10 2011 116 367 A1, in which a so-called multiple-quantum-well LED (MQW LED) is used. Like all LEDs, the MQW LED also has a spectrum with a width of approx. 5% to 20% of the central wavelength, although it differs from conventional LEDs in that the form of the emission spectrum is largely independent from temperature. According to DE 10 2011 116 367 A1 the spectrum of the MQW LED is selected such that, with reference to the absorption spectrum of a gas to be measured, it has portions which undergo considerable absorption and other portions which undergo little or no absorption at all through the gas to be measured.

At the exit of a measuring cell, the light of the MQW LED shone through is divided by a suitably chosen wavelength-selective beam divider into two portions, in which little absorption is to be expected in a reference portion, and considerable absorption in another portion corresponding to the gas concentration of the gas to be measured. This has the advantage that hardly any dispersive effects occur due to the close proximity of the various frequency portions and that only a single light source generates the light for the actual measurement and for the reference measurement. The prerequisite for this is the temperature stability of the emission spectrum, which is not guaranteed with conventional LEDs. The disclosure of DE 10 2011 116 367 A1 should also be incorporated in its entirety into the present patent application.

SUMMARY

In contrast, it is the object of the present invention to provide a compact arrangement for measuring gas absorption, with which gas concentrations of a plurality of gases of a gas mixture can be measured with a high degree of accuracy and at great speed even under extreme environmental conditions.

This object is achieved by an arrangement for measuring gas concentrations in a gas absorption method according to claim 1.

In a gas absorption method according to the invention, light from light sources of various wavelengths in the visible region, the UV region and/or IR region, in particular LED light sources, is conducted through a measuring cell with a gas mixture to be analysed, in particular a mixture of $NO_2$, $SO_2$ and/or NO in air, and gas concentrations of gases of the mixture to be measured are determined via a measurement of an attenuation of the light conducted into the measuring cell at various wavelengths, due to absorption in the various gases of the gas mixture. The arrangement according to the invention comprises a plurality of light sources, of which different wavelength spectra are adjusted to absorption bands, absorption gaps and/or transition regions between absorption bands and absorption gaps of the gases to be measured, a measuring cell, at least one measuring receiver, by means of which a light intensity at one or a plurality of the wavelengths shone in can be measured at the measuring cell exit, and an evaluation apparatus which is designed to determine the gas concentrations from the light intensities measured.

According to the invention, this arrangement is further developed in that the measuring cell has a narrow, longitudinally-extended beam path with an entrance-side opening diameter B and an absorption length L with L>B, in particular L>5·B, in particular L>10·B, wherein the measuring cell has a gas inlet and a gas outlet, wherein a plurality of light sources of different wavelength spectra is grouped into a first light source group, wherein an optical homogeniser is interposed between the first light source group and the measuring cell, wherein, in particular, the homogeniser is coupled to the light source group directly or via a common optical assembly.

Within the context of the present invention, a direct coupling means a coupling to an air gap or an optical medium, for example an optical adhesive, if applicable also a plurality of optical adhesive points. A suitable common optical assembly can be a collecting lens or lens group for example, which receives the light of all the light sources of the light source group together and conducts it to the homogeniser. A holomirror or a multiple lens array arranged in front of the light source group is also one such suitable common optical member. However, individual optical fibres for example, each of which is only coupled to one light source of the light source group, do not belong thereto.

The optical homogeniser is, in particular, a light conductor, or is designed as such. Furthermore, the optical homogeniser is in particular designed in the shape of a rod. Finally, it is in particular provided that the optical homogeniser is a rod-shaped light conductor, or is designed as such.

The invention is based on the fundamental idea that fast measurement of quickly-changing gas concentrations is only possible in very small measuring volumes, of which the gas content is also exchanged very quickly. Otherwise a slow exchange of the measuring gas in the measuring cell would cause quick changes of the gas concentrations to be washed out. However, as a matter of principle, a high degree of accuracy requires considerable length of absorption. This can be realised by a considerable length of the measuring cell itself on the one hand, and, on the other, by single or multiple mirroring in the measuring cell. In order to keep the measuring volume small at the same time, a narrow or respectively slim, longitudinally-extended shape of the beam path in the measuring cell has been selected according to the invention. The shape of the measuring cell should be adapted to the beam path as well as possible, in order to have as little dead volume as possible outside the beam path.

A further decisive factor for a high degree of measuring accuracy lies in the fact that as great a quantity of light as possible must be brought through the measuring cell to a receiver. In this case, with a narrow, longitudinally-extended measuring cell, it is a challenge to get most of the light sent from the light source into the measuring cell at all. In order to guarantee this, the majority of the light sources, in particular LEDs, are first grouped into a very small, compact light source group. This forms a small "multi-coloured" light source. The individual light sources of the light source group should be arranged as close to each other as possible in order to have as little dead area between them as possible, and thereby to have a high ratio of luminous to non-luminous area.

The emission area of the light source group and the radiation angle of the light source group define the available phase space of the light radiated, which should be brought into the measuring cell in as much of its entirety as possible, in order to guarantee a high degree of measuring accuracy. It should be noted that the beam path in the measuring cell spans a very small phase space. The light source group should have a small total emission area accordingly because, in this way, only a small phase space is populated or respectively generated from the start. A loss of light power and a certain selection and reduction of the phase space takes place in the homogeniser which hereby adapts the phase space taken up by the light let through to the phase space of the beam path of the measuring cell, wherein optical assemblies of lenses or mirrors can still be used if applicable. The provided light originally emitted is thus coupled into the measuring cell with a small beam path diameter, with only comparatively small losses. Hence the small diameter is conducive to a small measuring volume and a high temporal resolution of the measurement wherein the starting power of the light sources can be kept comparatively low at the same time.

Due to the combining of a plurality of individual light sources into one light source group, in this case this is not a continuous phase space, with the result that every incision through apertures or other obstacles can affect the combination and distribution of the various wavelength spectra at great cost to the intensity of individual wavelengths or respectively light sources. Since gas absorption measurements in gas mixtures also include the measurements of the relative strengths of the transported light of various colours or respectively wavelengths, such a selective effect would falsify the results. For this reason, according to the invention, a homogeniser is provided, which ensures that the available phase space, that is, the spatial distribution and angle distribution of the individual beams of light, is populated as uniformly as possible by all the wavelengths shone in, so that unavoidable incisions are not selectively affecting individual wavelengths. For this purpose the homogeniser collects the light of the various LEDs of the light source group, mixes its places of origin uniformly and radiates the light uniformly with as relatively small an aperture or respectively entrance opening as possible, wherein the light losses of the transmission from the sources to the target aperture or respectively target opening should be as small as possible. Such components are small, robust and cost-effective to produce and allow miniaturisation in contrast to the glass fibres used hitherto, which moreover still require fibre couplers and mode mixers. Any intensity losses produced by the homogeniser if applicable are acceptable compared to the afore-mentioned advantage.

The combination of features of the slim or respectively narrow beam path in the measuring cell together with the multi-coloured light source group grouped in a small space or respectively over a small surface and the homogeniser interposed therebetween now allows combining for the first time the high resolution and accuracy of a gas absorption measuring process with a miniaturisation necessary for a short measuring time, without having to compromise on measuring accuracy.

The diameter of the light source group can be smaller than an area of the opening diameter B of the beam path of the measuring cell, in particular less than a third of the area of the opening. Further, it can be an advantage if the homogeniser has an area on the side of the first light source group, which substantially corresponds to an area of the first light source group, in particular does not differ from the area of the first light source group by more than 40%. This design allows particularly great miniaturisation since the homogeniser with the corresponding proportions can be placed directly on the light source group and can transmit most of the light emitted. A somewhat less miniaturised embodiment is achieved if the entrance area of the homogeniser is much larger than the area of the first light source group, in particular more than twice as large. This embodiment is then advantageous if the construction necessitates a space between light source group and homogeniser.

An exit-side diameter $D_2$ of the homogeniser on the side of the measuring cell is preferably smaller than the opening diameter B of the beam path of the measuring cell.

The evaluation apparatus is a programmable data processing system with signal inputs and signal processing units or a digital signal processor (DSP) or microcontroller with upstream analog-digital converters or another analysers normally used for measuring purposes.

Using the arrangement according to the invention, measuring accuracies in the ppm range and smaller with repeated measuring rates of 10/s to 100/s are achievable.

In an advantageous development the first light source group comprises LED light sources with a characteristic radiation angle and the LED light source group is arranged in front of the homogeniser such that, having passed through the common optical assembly if applicable, a radiation cone of the LED light sources of the first light source group enters the homogeniser substantially in its entirety. The radiation cone comprises most of the light emitted and, after a definition, the angle which is enclosed by the lateral points with half the maximum light strength. This measure ensures that intensity losses are kept as small as possible during entry into the homogeniser. This contributes to achieving a high degree of measuring accuracy.

Preferably, the homogeniser is designed as a shaped, transparent solid light conductor on the basis of total reflection on the surface or of refractive index gradients in the substrate or as a hollow reflector arrangement with a transparent medium in the interior, in particular, a transparent gas or vacuum, and reflective lateral boundary surfaces, wherein the homogeniser is shaped linear or curved with a circular, oval or polygonal cross-section. In particular, the homogeniser is six-sided in cross-section. The available phase space in these homogenisers is populated increasingly uniformly by means of multiple reflection or multiple refraction. The occupancy of the phase space is further concentrated if the homogeniser advantageously changes, in particular tapers, in the cross-section towards the measuring cell.

Homogenisation is preferably further improved by arranging defects in or on the homogeniser, in particular, imperfections in the substrate, dispersing bodies in a mirror cavity or rough patches on boundary surfaces or mirror surfaces. Such defects result in considerable dispersion of the light. The considerable homogenisation achieved thereby is achieved at the expense of a greater loss of light intensity due to dispersion from the homogeniser, however the advantage of much greater homogenisation of the incident light can more than make up for the loss of available light intensity.

At its entrance opening, the measuring cell has and/or a member of the arrangement arranged adjacent to the measuring cells has a combined light inlet and light outlet window, and, facing the light inlet window and light outlet window, a light-reflecting wall or, alternatively, a light inlet window and a light outlet window respectively, with or without reflecting walls between the light inlet window and the light outlet window, wherein the light inlet window or light inlet windows and/or light outlet window or light outlet windows, in particular is or are inclined compared to a longitudinal extension of the measuring cell. The example of the combined light inlet window and light outlet window with the light-reflecting, that is mirroring, wall describes the case of a reflection cell, the other example that of a transmission cell.

The closure of the measuring cell by windows enables separation of the measuring cell from the remaining optical measuring structure, whereby it can be exchanged, cleaned, serviced and replaced. A diagonal positioning of the windows reduces disturbing reflections and is mechanically favourable for insertion into a structure. Fluidic dead volumes are likewise reduced. The measuring cell can also be taken out of the structure in its entirety, so that, if applicable, a simple exchange is possible for maintenance or cleaning purposes.

Hence, according to a further embodiment it is provided that the measuring cell can be taken out. In particular, the measuring cell can be dismantled without tools.

For calibration purposes, it is advantageous if the measuring cell is replaced by a calibration cell with defined wavelength-dependent absorption, which saves on expensive calibration gases. If the window or windows are not arranged on the measuring cell itself but on an adjacent member of the arrangement, the measuring cell consists of one pipe which, by means of a seal, is inserted sealed gas-tight opposite the window or windows. This variant has the advantage that the windows can be cleaned right in the arrangement and the remaining arrangement protected from cleaning liquid. This results in a modular, in particular hermetic, arrangement.

The gas inlet and the gas outlet are preferably arranged offset parallel to the diameter of the measuring cell to enable the gas to be exchanged swiftly.

If advantageously, at the entrance and/or at the exit of the measuring cell, is or are arranged one or a plurality of in particular wavelength-selective beam dividers, with which light of different light sources of the first light source group and/or a second light source group is conducted to two or more different measuring receivers, it is possible to once again separate the various wavelengths independently of each other, which the various light sources of the light source group have emitted, and which are designed for absorption bands and absorption gaps of various measuring gases, and to measure the attenuation at these wavelengths.

The object on which the invention is based is also achieved by an arrangement for measuring gas concentrations in a gas absorption method in which light from light sources of various wavelengths in the visible region, the UV region and/or IR region, in particular LED light sources, is conducted through a measuring cell with a gas mixture to be analysed, in particular a mixture of $NO_2$, $SO_2$ and/or NO in air, and gas concentrations of gases of the gas mixture to be measured are determined via a measurement of an attenuation of the light conducted into the measuring cell at various wavelengths due to absorption in the various gases of the gas mixture, wherein the arrangement comprises a plurality of light sources with different wavelength spectra, a measuring cell and a plurality of measuring receivers, by means of which light intensities at a plurality of emitted wavelengths can be measured at the exit of the measuring cell, which is developed in that the measuring cell has openings at each of its two ends and a first light source group and a second light source group, each with one light source or a plurality of light sources grouped together, are comprised, the light of which is conducted through the measuring cell on two beam paths, which are independent of each other, in particular in opposite directions to each other and, at the exit of the measuring cell, the light of both beam paths exiting the measuring cell is respectively conducted through in particular wavelength-selective beam dividers to measuring receivers, wherein at least one of the light source groups together with the beam path and measuring cell belonging thereto is formed as aforementioned arrangement according to the invention.

This arrangement according to the invention comprises the afore-described arrangement according to the invention completely and adds yet a further beam path and a further light source thereto. This second light source group can comprise a single light source, whereby a further wavelength for a further measuring gas of the gas mixture is added to the arrangement. The second light source group can also comprise a plurality of different light sources.

In principle, the arrangement according to the invention has the advantage that a plurality of gases can be measured in one and the same measuring volume, which increases the measuring accuracy since spatial and dynamic errors are prevented with the distribution of gas over a plurality of measuring cells. For this the two beam paths preferably partly or wholly overlap in a measuring volume of the measuring cell.

Measuring a plurality of gases by means of LED spectroscopy requires a plurality of light sources which can be coupled into the measuring cell from different directions, in order to enable temporally parallel measuring with little crosstalk. This is in particular provided with a combination of different measuring methods, such as those known in DE 10 2008 064 173 A1 and DE 10 2011 116 367 A1. Miniaturisation is used in place of the expensive, large glass fibres used in DE 10 2008 064 173 A1, since the required LEDs are positioned very close to each other and the light emitted is only captured and homogenised by one homogeniser and then divided into a path to measure the gas and a reference path via an external beam divider, for example a semipermeable mirror.

If, for example, both beam paths lead through the measuring cell in opposite directions, the measurements with the first beam path and the second beam path are decoupled ideally, which is especially advantageous if the wavelengths of the light sources used lie close together. However, there are other possibilities for substantially decoupling the beam paths from each other, for example defining various regions of the measuring cell, which are radiated by the individual beam paths or from angles at which the beam paths enter the measuring cell.

In a preferred development, both light source groups, each together with the beam path and the measuring cell belonging to it, are designed as afore-described arrangements according to the invention, wherein the measuring cell is common to both arrangements. Alternatively and likewise preferably one or respectively the second light source group comprises at least one MQW LED with a temperature-stable emission spectrum and, at the exit to the measuring cell, the beam path belonging to the second light source group comprises a wavelength-selective beam divider and two measuring receivers, wherein the wavelength-selective beam divider is configured to split the emission spectrum of the MQW LED into two or more portions and to conduct the portions separated from each other to the two measuring receivers.

In the latter case the partial measuring arrangement with the MQW LED substantially corresponds to the one which is known from DE 10 2011 116 367 A1 of the applicant. This version is particularly well suited to gases with narrow-band absorption spectra, such as nitrogen monoxide (NO). Filters such as this can be cut-off filters or bandpass filters.

In the context of the present description, a "wavelength-selective beam divider" means both an individual beam divider which divides in a wavelength-selective manner and a group of optical structural components. A group of optical structural components such as this comprises for example a beam divider which is not wavelength-selective, and at least two filters. One of the filters is provided in each of the divided beam paths in the direction of the incident light following the beam divider. The filters are cut-off filters or bandpass filters for example, which provide the functionality of wavelength selection.

The emission spectrum of the at least one MQW LED and a wavelength characteristic of the wavelength-selective beam divider are preferably adjusted to an absorption spectrum of a gas to be measured, such that a first portion of the emission spectrum of the MQW LED undergoes a greater absorption in the gas than a second portion. The light of the one MQW LED is thereby split into a measuring portion and a reference portion. Systematic effects are thus ideally suppressed. Also, if the reference portion is not entirely without absorption, these emission spectra of the MQW LED and the gas absorption spectra of the gases to be measured are indeed known, so that measuring in the measuring portion and in the reference portion can be extrapolated to the ideal scenario of non-absorption, which results in the gas concentration to be determined.

If the arrangement preferably comprises a pressure measuring device and/or temperature measuring device, which is connected to the measuring cell in order to measure a pressure and/or a temperature of the gas mixture in the measuring cell, wherein the evaluation apparatus is designed to take into account the influence of a measured level of pressure or of pressure fluctuations and/or of the temperature or temperature fluctuations on the light absorption or the gas concentrations when determining the gas concentrations, if applicable to extrapolate them to a normal pressure and/or a normal temperature, it is possible to take into account environmental effects when determining the gas concentrations, which have their own effect on the attenuation of the light. These are especially the pressure of the gas mixture and the temperature.

In an advantageous development measuring gas is conducted from a main gas flow into the measuring cell in a secondary flow process and, after passing through the measuring cell, conducted back into the main gas flow again or released into the surrounding air. This secondary flow process makes it possible to arrange the arrangement at a greater distance from surroundings which are detrimental to the light sources and measuring receiver. For example, this is the case in vehicle engines, in particular diesel engines.

If a greater distance of the light sources or the measuring receiver from the measuring cell is desired, the light is preferably coupled into the measuring cell and/or the light is coupled out of the measuring cell, by using additional light conductors. If the measuring volume should lie directly in detrimental surroundings, further increasing the distance of the measuring receiver, light sources and electronics from the measuring cell is desired. For this, the light is preferably coupled into the measuring cell and/or the light is coupled out of the measuring cell, by using additional light conductors.

Further features of the invention become apparent from the description of embodiments according to the invention together with the claims and the attached drawings. Embodiments according to the invention can comply with individual features or a combination of a plurality of features.

BRIEF DESCRIPTION OF DRAWINGS

Without being restricted to the general idea of the invention, the invention is described below by means of exemplary embodiments with reference to the drawings, and the drawings are expressly referred to with respect to all the details according to the invention, which are not explained in greater detail in the text. In the figures.

DETAILED DESCRIPTION

In each of the drawings the same members and/or parts, or members and/or parts of the same type, are provided with the same reference numbers so that a re-introduction is omitted.

Figure 1A:
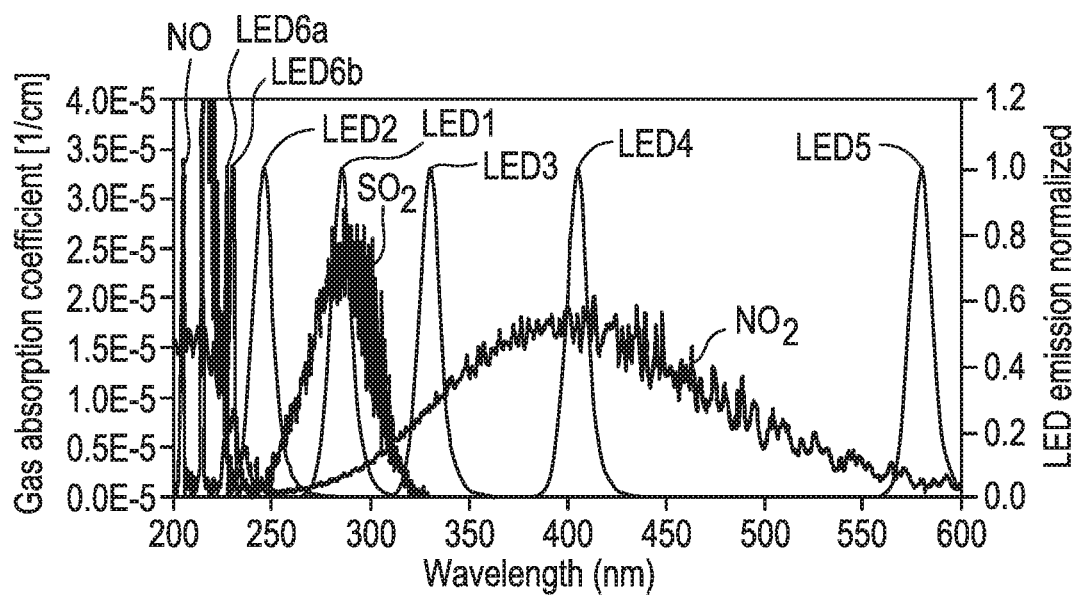
FIGS. 1a), b) show emission spectra and absorption spectra of measuring gases and LEDs

In FIGS. 1a) and 1b) each of the absorption spectra of the gases nitrogen monoxide (NO), sulphur dioxide ($SO_2$) and nitrogen dioxide ($NO_2$) are shown together with the emission spectra of six different LEDs, which are arbitrarily normalised to a common maximum emission. A gas mixture such as this occurs, for example, in the exhaust gas of vehicles for example, the ratios of NO and $NO_2$ depending on temperature. The wavelengths begin at 200 nm, that is, in the UV region and go as far as 600 nm in FIG. 1a). The section in FIG. 1b) is completely located in the UV region between 200 nm and 270 nm.

The absorption spectrum of $NO_2$ is particularly broadband and has a maximum at approx. 400 nm. Both the LED3 at 330 nm and the LED4 at approx. 405 nm undergo a significant absorption in $NO_2$. The longer-wave LED5 at 580 nm can serve as a reference since it undergoes very much less absorption in $NO_2$. The narrower absorption spectrum of $SO_2$ with a width of approx. 60 nm is located around the maximum at 285 nm in the UV region. The LED1 and its emission spectrum are centred thereon. A further LED2 and its emission spectrum are centred around a maximum at approx. 246 nm and lie in a local minimum of the absorption spectra of all three gases shown. Hence this LED2 wavelength is suited to being a reference wavelength and has the further advantage compared to LED5 for example, in that not only is the absorption low, but also the dispersive effects relative to the wavelengths of, for example, LED1 and LED3, also LED 4, are less.

Figure 1B:
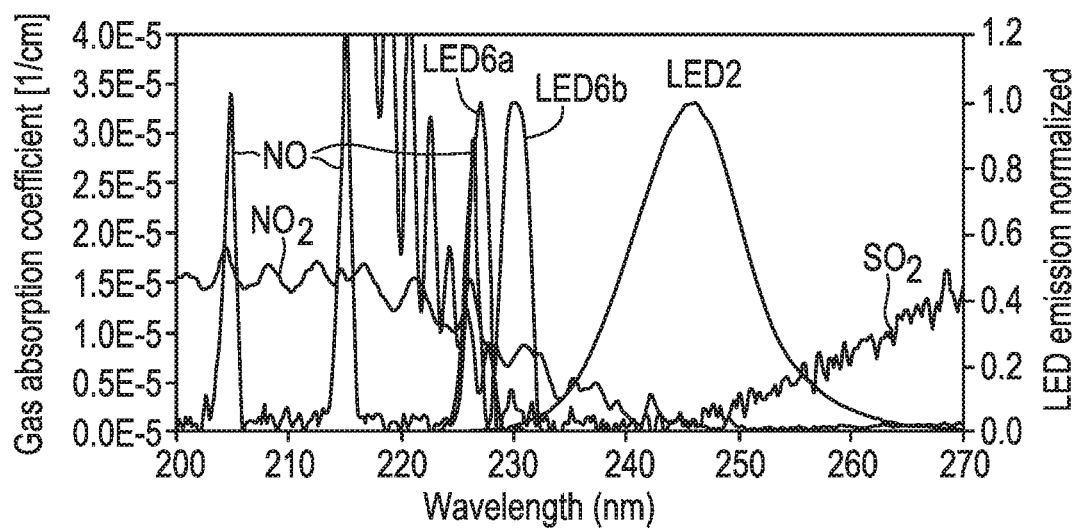

As can be seen clearly from FIG. 1b), the NO absorption spectrum consists of a plurality of narrow bands with widths of few nanometres at 205 nm, 215 nm and 226 nm. An MQW LED labelled LED6 generates light in a region with a width of approx. 8 nm around 248 nm. The spectrum is divided into two regions labelled LED6a and LED6b, which are generated with steep edge, by splitting in a wavelength-selective interferometric beam divider. In this case the shorter-wave portion LED6a has a large overlap with an absorption peak of NO at 226 nm, whereas the longer-wave portion LED6b has scarcely any overlap with the absorption peak and can therefore be used as a reference from the same light source. The principle is illustrated more clearly in FIG. 8 below.

Figure 2:
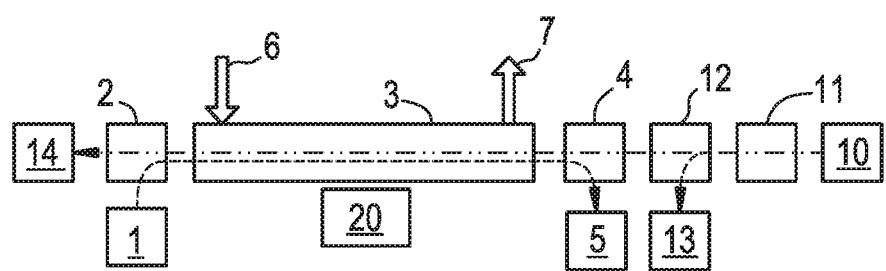
FIG. 2 shows a schematic representation of an arrangement according to the invention.

FIG. 2 shows a schematic presentation of an arrangement according to the invention, in the centre of which stands a measuring cell 3 with a measuring gas or respectively gas mixture. The measuring cell 3 is a slim, elongated, for example cylindrical measuring cell 3, which has the advantage that, with little volume and therefore a possible high exchange rate of the measuring gas, a considerable absorption length is achievable. For this, the measuring cell 3 has a gas inlet 6 and a gas outlet 7.

A light source group 10 is shown on the right-hand side, in which a plurality of light sources of various colours, for example LEDs, are grouped in a small space according to the invention. The light they emit reaches the measuring cell 3 through a homogeniser 11, which will be explained in still greater detail in the following, and via beam divider 12, 4. The beam divider 12 can fulfil the function of conducting a part of the light emitted into a reference measuring receiver 13 as a reference. Moreover, the beam divider 12 can, but does not have to, be wavelength-selective. The remaining portion of the light from the light source group 10 passes through the entire length of the measuring cell 3, undergoes a wavelength-dependent absorption in the gas mixture in so doing and reaches the measuring receiver 14 at the other end, which is designed to measure the intensity of the light falling onto it. The attenuation is then calculated or determined by means of comparison with a target value or by means of comparison with the intensity in reference measuring receiver 13 and the gas concentrations of the gases to be investigated determined therefrom.

Connected to the measuring cell 3 is a pressure measuring device and/or temperature measuring device 20, which measures pressure and/or temperature of the gas in the measuring cell 3 and transmits it to the evaluation apparatus not shown, which, from this, can make corrections to the determination of the gas concentrations.

The invention according to the arrangement according to FIG. 2 has a second measuring path which is oriented in the opposite direction to the first, afore-described measuring path. The second measuring path starts with a light source group 1, which, at its simplest, comprises or has a single MQW LED. A plurality of MQW LEDs can also be comprised or mixtures of various LEDs with or without MQW LED. The exemplary embodiment shown comprises at least one MQW LED, for example LED6 of FIG. 1. A beam divider 2 directs the light of light source group 1, that is, the MQW LED, into the measuring cell 3 and separates the beam paths of the first measuring path and the second measuring path from each other. After passing through the measuring cell, a beam divider 4, which can be a wavelength-selective beam divider, again separates the two measuring paths or respectively beam paths from each other and directs the light from light source group 1 into a measuring arrangement with a measuring receiver 5. This measuring arrangement can comprise a further beam divider which performs a division with a steep edge in accordance with the description above and FIG. 8 here below. In this case two optical measuring receivers, for example photodiodes, are used.

A common beam divider can also be used in place of two beam dividers 4, 12, which is accordingly designed to decouple both beam paths in a wavelength-selective manner, for which it should be partly transparent and partly reflecting for the wavelengths of the first light source group 10. In such a case the measuring receivers 5 and 13 are arranged on opposite sides of the main beam path.

Figure 3:
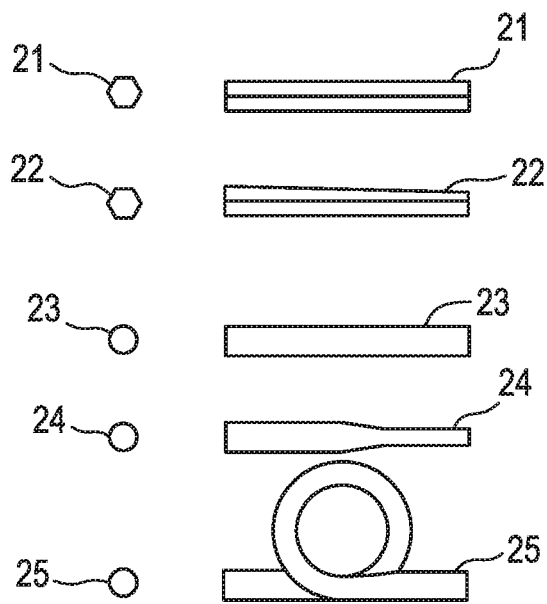
FIG. 3 shows examples of homogenisers according to the invention.

In FIG. 3 various examples of homogenisers 21 to 25 according to the invention are shown schematically. The homogeniser 21, which is shown in the cross-section on the left-hand side and from the side on the right-hand side, is a conventional solid light conductor with a six-sided or respectively hexagonal cross-section. The homogeniser 22 differs from this in that it tapers from the entrance towards the exit, which contributes to greater homogenisation. Hexagonal cross-sections such as this have the property that more light losses occur on the abutting edges between two smooth surfaces whereas they are more distributed over the entire area in round cross-sections.

In contrast to the homogeniser 2, the homogeniser 23 has a round cross-section. Although it tapers, the homogeniser 24 also has a round cross-section. Finally, although it curves through 360°, the homogeniser 24 has a round cross-section and a constant diameter, which results in considerable homogenisation. All these are solid homogenisers made out of glass or plexiglass for example.

Figure 4:
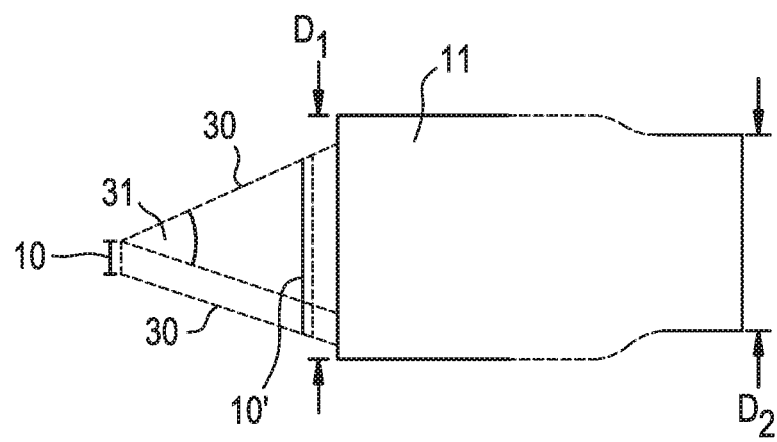
FIG. 4 shows a schematic representation of a part of an arrangement according to the invention.

In FIG. 4 the combination of the light source group 10 and the homogeniser 11 is shown schematically. The light source group 10 has a plurality of single LEDs of various wavelengths or respectively colours, which are indicated as short dashes and placed next to each other in a small space. This light source group 10 will usually have a diameter of less than 1 to 2 mm. Like most LEDs, these LEDs have a radiation angle 31, which leads to a complete radiation cone 30 of the light source group 10, which exits the entire area of the light source group 10 and broadens towards the entrance area of the homogeniser 11. The distance between light source group 10 and the entrance area of homogeniser 11 has been selected such that, when entering homogeniser 11, the cone 30 has a diameter which is smaller than the opening aperture $D_1$ of the homogeniser 11. Inside the homogeniser, which tapers to a smaller diameter $D_2$ towards the exit, light is conducted with no or little loss of intensity.

A relatively larger light source group 10', which is arranged much nearer to the homogeniser 11, also spans the same radiation cone 30. For the purpose of miniaturisation the choice of making the homogeniser 11 roughly as large as large as the light source group 10' and placing it right in front of the light source group 10' accordingly is more favourable.

Figure 5:
FIG. 5 shows a schematic representation of a homogenisation without dispersion centres.
Figure 6:
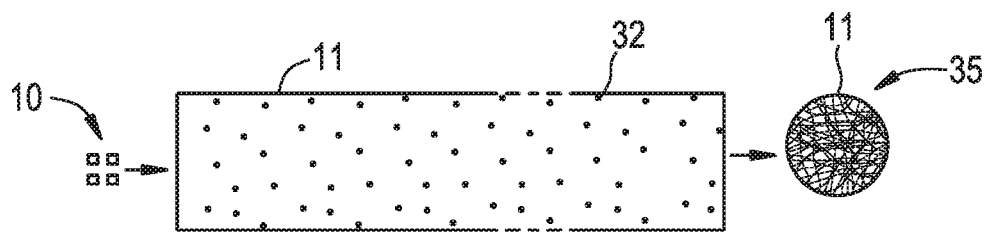
FIG. 6 shows a schematic representation of a homogenisation with dispersion centres, FIGS. 7a)-d) show schematic representations of light conduction principles of homogenisers according to the invention

Each of FIGS. 5 and 6 show how the phase space, in this case the occupancy of the spatial distribution, is compensated by the respective homogeniser 11. The spatial distribution of the light emitted is at first the spatial arrangement of the LEDs of the light source group 10, shown on the left in each of FIGS. 5 and 6. After passing through the homogeniser, which is provided without defects in FIG. 5 and with defects 32 in FIG. 6, all the LEDS, which substantially cover the exit area of the homogeniser 11 uniformly, are reflected in many ways in the first case. However, the individual LEDs can still be substantially identified as such. If, as in FIG. 6, defects 32 are present, the additional dispersion of the light in the homogeniser 11 generates complete blurring, such that the individual light sources are no longer identifiable. However, this is at the expense of a loss of intensity due to the light dispersed out of homogeniser 11. In place of defects 32 the exterior surface can also be roughened, such that defects arise in the total reflection, which have a similar effect to embedded defects 32.

Figure 7A:
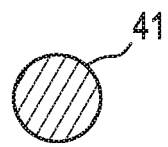

FIGS. 7a) to d) again show cross-sections of various embodiments of homogenisers which can be used according to the invention. According to FIG. 7a) the homogeniser 40 has a round cross-section and is solid. In this case, light conduction takes place by means of total reflection on the outer surface. The homogeniser 42 from FIG. 7 b) differs from this only in its shape which is hexagonal in this case. Here losses of light are concentrated on the edges between the individual lateral surfaces.

Figure 7B:
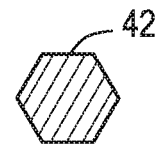
Figure 7C:
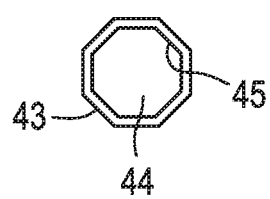
Figure 7D:
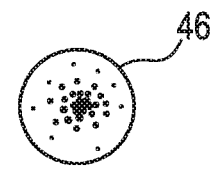

FIG. 7c) shows an example of the homogeniser 43 designed as a reflector arrangement of which the outer contours do not differ from those in FIG. 7b). However, it is hollow inside and has reflected interior surfaces 45 around its interior space 44. Finally, FIG. 7d) again concerns a solid homogeniser 46, which, unlike the exemplary embodiment of FIG. 7a), has a higher refractive index gradient in the centre than at the edge, so that light is conducted by means of refraction due to the refractive index gradients. Moreover, on the boundary surface to the surrounding air total reflection takes place.

Figure 8:
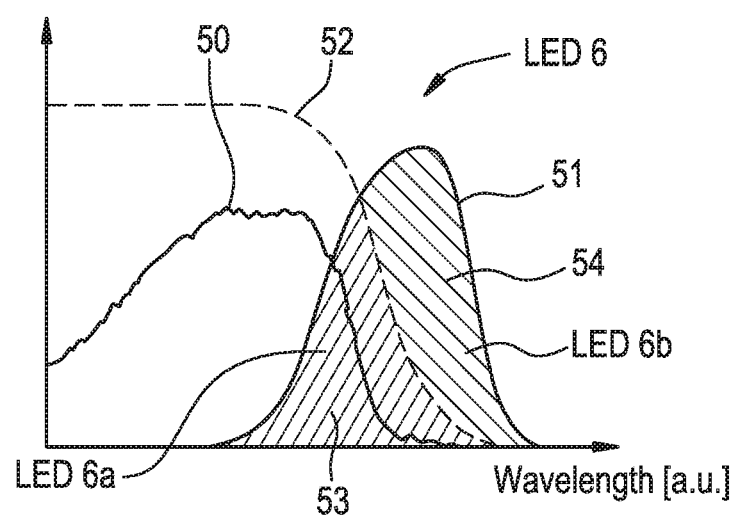
FIG. 8 shows the spectral overlapping principle and dividing principle when using MQW LED is to measure gas absorption.

In FIG. 8 the principle of path division with MQW LED is clearly illustrated schematically once more. A wavelength is again shown on the horizontal axis in arbitrary units, an absorption amplitude, transmission amplitude or an emission amplitude respectively given in arbitrary units on the vertical axis. The absorption spectrum of a measuring gas with a comparatively steep edge is labelled with reference number 50. The emission spectrum 51 of a MQW LED, for example LED6 in FIG. 1, is selected such that it only partially overlaps with the falling edge of the settling spectrum 50. Accordingly, a wave length characteristic of an interferometric beam divider with steep edge is drawn as a dashed line 52, the edge of which substantially divides the emission spectrum 51 into two parts which are transmitted to different measuring receivers, for example photodiodes. These two portions are shaded differently and labelled with reference numbers 53 and 54 for a signal portion and a reference portion. The signal portion 53 has a large overlap with the falling edge of absorption spectrum 50, whereas the reference portion 54 has hardly any overlap therewith. These portions 53 and 54 are labelled LED6a and LED6b in FIG. 1a) and FIG. 1b) and shown separated from each other, even though they originate from a single light source. A bandpass filter can also be used instead of the short-pass filter shown.

All the features mentioned, also the features to be inferred from the drawings alone, as well as individual features which are disclosed in combination with other features, are regarded as essential to the invention individually and in combination. Embodiments according to the invention can also be complied with by individual features or a combination of a plurality of features. Within the context of the invention, features which are described with "in particular" or "preferably" are to be understood to be optional features.

REFERENCE LIST

1 Light source group with MQW LED
2 Spectral beam divider
3 Measuring cell
4 Spectral beam divider
5 Measuring receiver
6 Gas inlet
7 Gas outlet
10, 10' Light source group
11 Homogeniser
12 Beam divider
13 Reference measuring receiver
14 Measuring receiver
20 Pressure and/or temperature measuring device
21-25 Homogeniser
30 Radiation cone
31 Radiation angle
32 Defects
34, 35 Intensity distribution at the exit of the homogeniser
41 Homogeneous round homogeniser
42 Homogeneous hexagonal homogeniser
43 Inwardly reflected homogeniser
44 Cavity
45 Inward reflection
46 Homogeniser with refractive index gradient
50 Absorption spectrum of a gas
51 Emission spectrum of an MWQ LED
52 Wave length characteristic of an interferometric beam divider
53 Signal portion
54 Reference portion

What is claimed is:

1. An arrangement for measuring gas concentrations in a gas absorption method in which light from light sources of various wavelengths in the visible region, the UV region and/or IR region, is conducted through a measuring cell with a gas mixture to be analysed, and gas concentrations of gases of the gas mixture to be measured are determined via a measurement of an attenuation of the light conducted into the measuring cell at various wavelengths due to absorption in the various gases of the gas mixture, the arrangement comprising:

a plurality of light sources having different wavelength spectra that are adjusted to absorption bands, absorption gaps and/or transition regions between absorption bands and absorption gaps of the gases to be measured, wherein the plurality of light sources is grouped into a first light source group with a first plurality of the light sources of different wavelength spectra and a second light source group with one or a second plurality of the light sources of different wavelength spectra, a measuring cell having openings at each of its two ends, wherein the light of the first light source group and of the second light source group is conducted on two independent beam paths through the measuring cell and the light of both beam paths exiting the measuring cell respectively conducted through wavelength-selective beam dividers to corresponding first and second measuring receivers, wherein each of the first and second measuring receivers measures, at an exit of the measuring cell, a light intensity in one or a plurality of the wavelengths emitted, and an evaluation apparatus configured to determine the gas concentrations from the measured light intensities, wherein at least one beam path through the measuring cell is a narrow, longitudinally-extended beam path with an entrance-side opening diameter B and an absorption length L with L>B, wherein the measuring cell has a gas inlet and a gas outlet, wherein an optical homogeniser is interposed between the first light source group and the measuring cell.

2. An arrangement according to claim 1, wherein the light sources of the first light source group are LED light sources with a characteristic radiation angle, and the LED light sources of the first light source group are arranged in front of the homogeniser, such that a radiation cone of the LED light sources of the first light source group enters the homogeniser substantially complete.

3. An arrangement according to claim 2, wherein the LED light sources of the first light source group are arranged in front of the homogeniser, such that a radiation cone of the LED light sources of the first light source group, after passing through a common optical assembly, enters the homogeniser substantially complete.

4. An arrangement according to claim 1, wherein the homogeniser is a shaped, transparent solid light conductor on the basis of total reflection on the surface or of refractive index gradients in the substrate or as a hollow reflector arrangement with a transparent medium in the interior, and reflective lateral boundary surfaces, wherein the homogeniser is shaped linear or curved with a circular, oval or polygonal cross-section.

5. An arrangement according to claim 4, wherein the homogeniser alters, in the cross-section in the direction towards the measuring cell.

6. An arrangement according to claim 1, wherein defects are arranged in or on the homogeniser.

7. An arrangement according to claim 6 wherein defects are: imperfections in the substrate, dispersion bodies in a mirror cavity, rough patches on boundary surfaces, or rough patches on mirror surfaces.

8. An arrangement according to claim 1, wherein at its entrance opening, the measuring cell and/or a member of the arrangement adjacent to the measuring cell has a combined light inlet and light outlet window, and, facing the light inlet window and light outlet window, a light-reflecting wall.

9. An arrangement according to claim 1, wherein, at the entrance and/or at the exit of the measuring cell, is arranged one or a plurality of beam dividers, with which light of different light sources of the first light source group and/or a second light source group is conducted to two or more different measuring receivers.

10. An arrangement according to claim 1, wherein the two beam paths partly or wholly overlap in a measuring volume of the measuring cell.

11. An arrangement according to claim 1, wherein:
the first light source group is adjacent an opening at a first end of the measuring cell; and
the second light source or the second light source group is adjacent an opening at a second end of the measuring cell.

12. An arrangement according to claim 1, wherein the one light source or at least one of the light sources of the second light source group is a MQW LED with a temperature-stable emission spectrum, and
the beam path belonging to the second light source group comprises a wavelength-selective beam divider and two measuring receivers at the exit of the measuring cell, wherein the wavelength-selective beam divider is configured to split the emission spectrum of the MQW LED into two or more portions and to conduct the portions separated from each other to the two measuring receivers.

13. An arrangement according to claim 12, wherein the emission spectrum of the at least one MQW LED and a wavelength characteristic of the wavelength-selective beam divider are adjusted to an absorption spectrum of a gas to be measured, such that a first portion of the emission spectrum of the MQW LED undergoes a greater absorption in the gas than a second portion.

14. An arrangement according to claim 1, further comprising a pressure measuring device and/or temperature measuring device connected to the measuring cell, the pressure measuring device and/or temperature measuring device configured in order to measure a pressure and/or a temperature of the gas mixture in the measuring cell, wherein the evaluation apparatus is configured to take into account the influence of at least one of:

a measured level of pressure, pressure fluctuations, the temperature, and temperature fluctuations, when determining the gas concentrations to extrapolate them to a normal pressure and/or a normal temperature.

15. An arrangement according to claim 1, wherein light is coupled into the measuring cell and/or light is decoupled out of the measuring cell, by using additional light conductors.

16. An arrangement according to claim 1 wherein the measuring cell can be taken out.

17. An arrangement according to claim 1, wherein the homogeniser, directly or via a common optical assembly, is coupled to the light source group.

18. An arrangement according to claim 1, wherein at its entrance opening, the measuring cell and/or a member of the arrangement adjacent to the measuring cell has a light inlet window and a light outlet window respectively, with or without reflecting walls between the light inlet window and the light outlet window, wherein the light inlet window or light inlet windows and/or light outlet window or light outlet windows, is inclined compared to a longitudinal extension of the measuring cell.

19. An arrangement according to claim 1, wherein the two beam paths are in opposite directions to each other.

* * * * *